(12) United States Patent  
Tsai (10) Patent No.: US 8,562,911 B2  
(45) Date of Patent: Oct. 22, 2013

(54) CENTRIFUGAL ROTOR AND METHOD FOR USING THE SAME FOR DELIVERING BIOLOGICAL SAMPLE

(75) Inventor: Ying-Lan Tsai, Taoyuan County (TW)

(73) Assignee: MEDI Medical Engineering Corp., Taoyuan County (TW)

( * ) Notice: Subject to any disclaimer, the term of this patent is extended or adjusted under 35 U.S.C. 154(b) by 473 days.

(21) Appl. No.: 12/700,751

(22) Filed: Feb. 5, 2010

(65) Prior Publication Data

US 2011/0195502 A1    Aug. 11, 2011

(51) Int. Cl.
*G01N 33/00* (2006.01)
(52) U.S. Cl.
USPC ............. 422/72; 422/400; 422/401; 422/402; 422/403
(58) Field of Classification Search
USPC ............................ 422/72, 400, 401, 402, 403
See application file for complete search history.

(56) References Cited

U.S. PATENT DOCUMENTS

| | | | |
|---|---|---|---|
| 5,061,381 A | 10/1991 | Burd | |
| 5,122,284 A | 6/1992 | Braynin et al. | |
| 5,160,702 A | * 11/1992 | Kopf-Sill et al. | ............... 422/72 |
| 5,173,193 A | 12/1992 | Schembri | |
| 5,186,844 A | 2/1993 | Burd et al. | |
| 5,242,606 A | 9/1993 | Braynin et al. | |
| 5,275,016 A | 1/1994 | Chatterjee et al. | |
| 5,304,348 A | 4/1994 | Burd et al. | |
| 5,403,415 A | 4/1995 | Schembri | |
| 5,409,665 A | 4/1995 | Burd | |
| 5,413,732 A | 5/1995 | Buhl et al. | |
| 5,457,053 A | 10/1995 | Burd et al. | |
| 5,472,603 A | 12/1995 | Schembri | |
| 5,478,750 A | 12/1995 | Bernstein et al. | |
| 5,518,930 A | 5/1996 | Burd | |
| 5,590,052 A | 12/1996 | Kopf-Sill et al. | |
| 5,591,643 A | 1/1997 | Schembri | |
| 5,599,411 A | 2/1997 | Schembri | |
| 5,624,597 A | 4/1997 | Buhl et al. | |
| 5,693,233 A | 12/1997 | Schembri | |
| 5,776,563 A | 7/1998 | Buhl et al. | |
| 5,998,031 A | 12/1999 | Buhl et al. | |
| 6,235,531 B1 | 5/2001 | Kopf-Sill et al. | |
| 6,251,684 B1 | 6/2001 | Buhl et al. | |
| 6,752,961 B2 | 6/2004 | Kopf-Sill et al. | |
| 6,818,415 B2 | 11/2004 | Chiang | |
| 7,177,767 B2 | 2/2007 | Ostoich et al. | |

* cited by examiner

*Primary Examiner* — Sam P Siefke
(74) *Attorney, Agent, or Firm* — CKC & Partners Co., Ltd.

(57) ABSTRACT

Disclosed herein is a centrifugal rotor for delivering and analyzing biological sample. Chambers within the centrifugal rotor is used to split a biological sample, which comprises biological cellular components and biological fluids, into separate parts under centrifugal force after the biological sample being diluted, metered and distributed by the centrifugal rotor.

16 Claims, 10 Drawing Sheets

CENTRIFUGAL ROTOR AND METHOD FOR USING THE SAME FOR DELIVERING BIOLOGICAL SAMPLE

BACKGROUND

1. Field of Invention

The present invention relates to generally to devices and methods for delivering and/or analyzing biological sample. More particularly, the present invention relates to a centrifugal rotor for delivering and analyzing biological sample.

2. Description of Related Art

Biological tests of blood plasma and other biological fluids frequently require that fluids be quickly divided into predetermined volumes for analysis in a variety of tests or assays. It is also frequently desirable to separate potentially interfering cellular components of the material from the biological fluid prior to testing. Such measurement and separation steps have previously been typically performed by centrifugation to separate, for instance, blood plasma from the cellular components, followed by manual or automated pipetting of predetermined volumes of the blood plasma into separate test wells. Such procedures are labor intensive and time-consuming. As a result, various automated systems and methods have been proposed for providing multiple aliquots of plasma suitable for testing in a more efficient manner.

A major advance in the analysis of biological fluids has been the use of centrifugal rotors. These rotors are designed to measure volumes of a biological fluid, such as blood, remove cellular components, and mix the fluid with an appropriate diluent for optical testing. Typically, the rotors provide a plurality of discrete volumes of sample in separate cuvettes in which the sample is optically analyzed.

The rotors capable of performing these functions should be capable of measuring and distributing relatively small volumes of liquid to a large number of cuvettes. The rotor design should be simple and amenable to low-cost manufacturing procedures. In particular, it is desirable for the rotors to be of unitary construction with no separable or movable parts. The present invention addresses these and other needs.

SUMMARY

In accordance with an aspect of the present invention, a centrifugal rotor includes a rotor body, which includes a sample application chamber, a diluent container, a mixing chamber, a distribution ring, at least one splitting cuvette and a react cuvette. The diluent container includes a diluent inside thereof. The mixing chamber is disposed radially outward from the sample application chamber and the diluent container for receiving fluid from thereof. The distribution ring is disposed radially outward from the mixing chamber and connected with the mixing chamber via a first siphon. The splitting cuvette is disposed radially outward from the distribution ring. Each splitting cuvette includes a relatively shallow cuvette and a relatively deep cuvette disposed radially outward from the relatively shallow cuvette. The react cuvette is connected with the relatively shallow cuvette via a second siphon.

According to another embodiment disclosed herein, the centrifugal rotor further includes a first delivery channel and a second delivery channel. The first delivery channel is interconnected between the second metering chamber and the application sample chamber for removing a sample fluid in the application sample chamber under centrifugal force. The second delivery channel is interconnected between the second metering chamber and the mixing chamber for removing the sample fluid in the second metering chamber under centrifugal force. The first delivery channel comprises a bubble-enhanced valve, a sacrificed valve, or a valve having a cross-section smaller than a cross-section of the second metering chamber and the application sample chamber. The second delivery channel comprises a bubble-enhanced valve, a sacrificed valve or a valve having a cross-section smaller than a cross-section of the second metering chamber and the mixing chamber.

According to another embodiment disclosed herein, the centrifugal rotor further includes a third delivery channel interconnected between the diluent container and mixing chamber for removing a diluent in the diluent container under centrifugal force, wherein the third delivery channel includes a bubble-enhanced valve or sacrificed valve.

According to another embodiment disclosed herein, the diluent container is a piston-regulated chamber.

According to another embodiment disclosed herein, the diluent container is an aluminum sealed diluent container.

According to another embodiment disclosed herein, the distribution ring includes two opposite first end and second end, the first end is connected to the first siphon, the second end is connected to the excess fluid dump, and the second end is radially outward from the first end.

According to another embodiment disclosed herein, the distribution ring is an arc with a corresponding center different from a center of the rotor body.

In accordance with still another aspect of the present invention, a method for using a centrifugal rotor to delivering a biological sample includes the step of using. chambers within single one centrifugal rotor to split a biological sample, which comprises biological cellular components and biological fluids, into separate parts under centrifugal force after the biological sample being diluted, metered and distributed by the single one centrifugal rotor.

According to an embodiment disclosed herein, the method further includes the step of using a distribution ring within the single one centrifugal rotor to distribute the biological sample into a plurality of splitting cuvettes, which are disposed radially outward from the distribution ring.

According to another embodiment disclosed herein, the method further includes the step of using a mixing chamber, which is disposed radially inward from the distribution ring, within the single one centrifugal rotor to dilute the biological sample.

According to another embodiment disclosed herein, the method further includes the step of using the splitting cuvette, which comprises a relatively shallow cuvette and a relatively deep cuvette disposed radially outward from the relatively shallow cuvette, so as to split the biological sample into separate parts under centrifugal force.

According to another embodiment disclosed herein, the method further includes the step of using a metering channel, which is interconnected between the distribution ring and the splitting cuvette, within the single one centrifugal rotor to meter the diluted biological sample.

According to another embodiment disclosed herein, the method further includes the step of using a first metering chamber, which is interconnected between the mixing chamber and the distribution ring, to meter the diluted biological sample.

In accordance with another aspect of the present invention, a centrifugal rotor includes a rotor body, which includes a sample application chamber, a diluent container, a mixing and splitting chamber, a distribution ring, a first metering chamber, a second metering chamber, a first excess dump and at least one cuvette. The mixing and splitting chamber is disposed radially outward from the sample application chamber and the diluent container for receiving fluid from thereof. The first metering chamber is interconnected between the mixing and splitting chamber and the sample application chamber. The second metering chamber is disposed radially outward from and connected with the first metering chamber. The first excess dump is connected with the second metering chamber. The distribution ring is disposed radially outward from the mixing and splitting chamber, and connected with the mixing and splitting chamber via a first siphon. The at least one react cuvette is disposed radially outward from and connected with the distribution ring.

According to another embodiment disclosed herein, the centrifugal rotor further includes a metering channel interconnected between the distribution ring and the react cuvette.

According to another embodiment disclosed herein, the centrifugal rotor further includes a valve interconnected between the metering channel and the react cuvette, wherein the valve is a bubble-enhanced valve, a sacrificed valve or a valve having a cross-section smaller than a cross-section of the metering channel and the react cuvette.

According to another embodiment disclosed herein, the centrifugal rotor further includes a second excess fluid dump, wherein the distribution ring is interconnected between the first siphon and the second excess fluid dump.

According to another embodiment disclosed herein, the centrifugal rotor further includes a first delivery channel and a second delivery channel. The first delivery channel is interconnected between the first metering chamber and the mixing and splitting chamber for removing a fluid in the first metering chamber under centrifugal force. The second delivery channel is interconnected between the diluent container and the mixing and splitting chamber for removing a diluent in the diluent container under centrifugal force. The first delivery channel comprises a bubble-enhanced valve, a sacrificed valve or a valve having a cross-section smaller than a cross-section of the first metering chamber and the mixing and splitting chamber. The second delivery channel comprises a sacrificed valve, a bubble-enhanced valve or a valve having a cross-section smaller than a cross-section of the diluent container and the mixing and splitting chamber.

According to another embodiment disclosed herein, the mixing and splitting chamber includes a chamber tail disposed radially outward from thereof.

According to another embodiment disclosed herein, the chamber tail is a relatively deeper area compared with the remaining area of the mixing and splitting chamber.

According to another embodiment disclosed herein, the diluent container is a piston-regulated chamber.

According to another embodiment disclosed herein, the diluent container is an aluminum sealed diluent container.

According to another embodiment disclosed herein, the distribution ring includes two opposite first end and second end, the first end is connected to the first siphon, the second end is connected to the second excess fluid dump, and the second end is radially outward from the first end.

According to another embodiment disclosed herein, the distribution ring is an arc with a corresponding center different from a center of the rotor body.

According to another embodiment disclosed herein, the distribution ring is part of a circle, which is concentric to a circumference of the rotor body.

According to another embodiment disclosed herein, the centrifugal rotor further includes at least one splitting cuvette disposed radially outward from the distribution ring. The splitting cuvette includes a relatively shallow cuvette and a relatively deep cuvette disposed radially outward from the relatively shallow cuvette.

According to another embodiment disclosed herein, the centrifugal rotor further includes a metering channel interconnected between the distribution ring and the splitting cuvette.

According to another embodiment disclosed herein, the centrifugal rotor further includes a valve interconnected between the metering channel and the splitting cuvette, wherein the valve is a bubble-enhanced valve, a sacrificed valve or a valve having a cross-section smaller than a cross-section of the metering channel and the splitting cuvette.

According to another embodiment disclosed herein, the splitting cuvette further comprises a neck, which has a smaller cross-sectional area than the relatively shallow cuvette and relatively deep cuvette has, interconnected between the relatively shallow cuvette and relatively deep cuvette.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE EMBODIMENTS

Reference will now be made in detail to the present embodiments of the invention, examples of which are illustrated in the accompanying drawings. Wherever possible, the same reference numbers are used in the drawings and the description to refer to the same or like parts.

Figure 1:
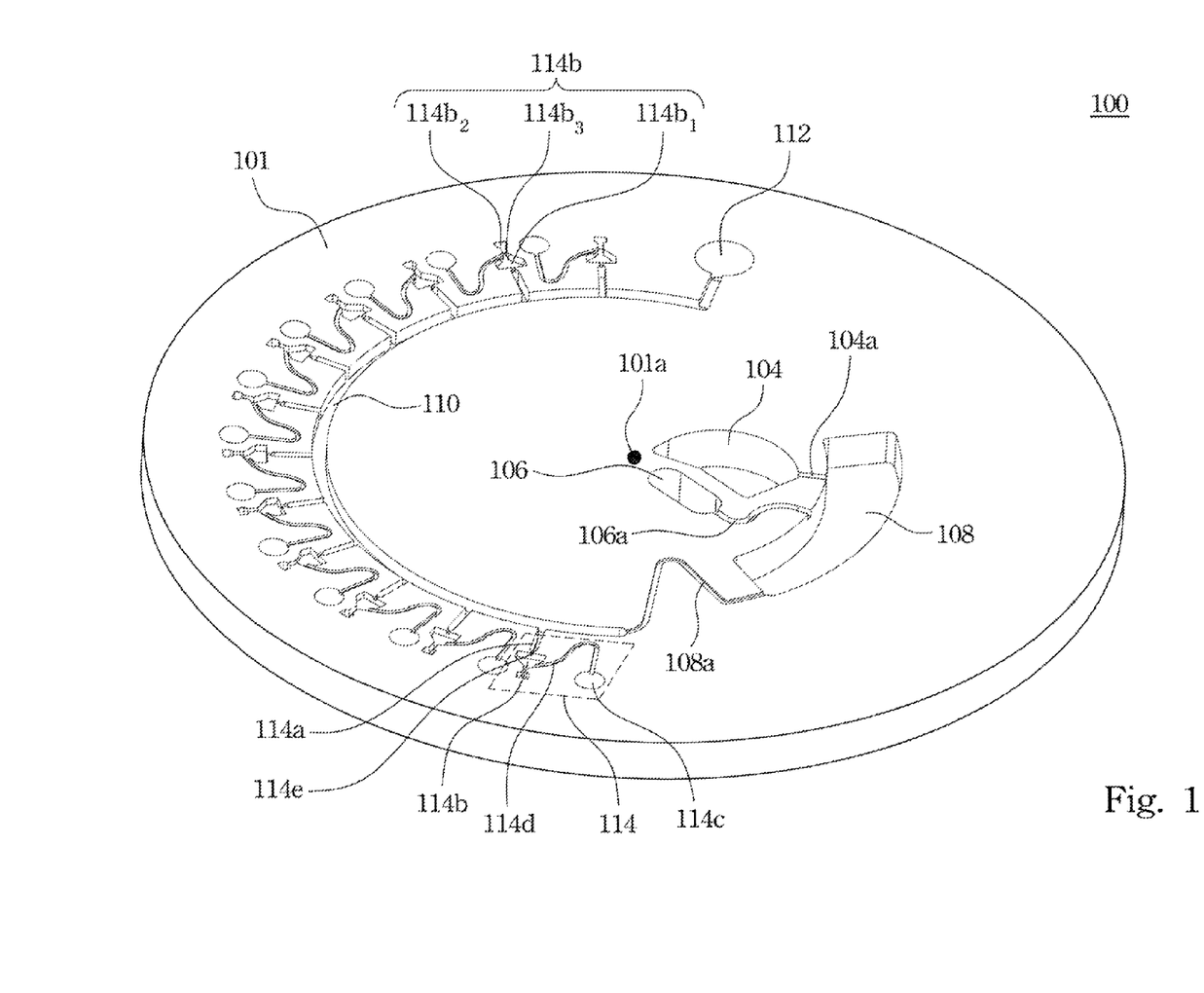
FIG. 1 illustrates a perspective view of a centrifugal rotor according to one embodiment of this invention.
Figure 2:
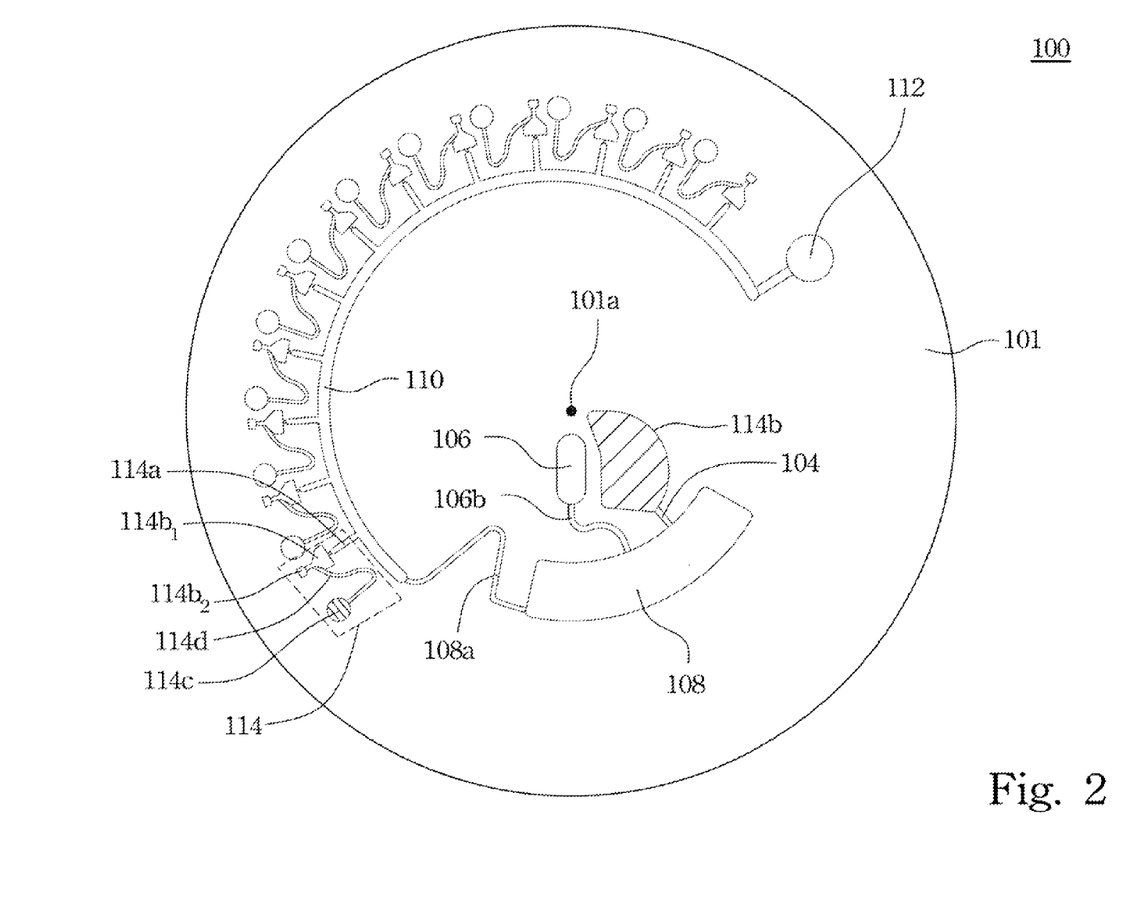
FIG. 2 illustrates a plan view of the centrifugal rotor in FIG. 1.

Referring FIG. 1 and FIG. 2, which respectively illustrate a perspective view and plan view of a centrifugal rotor according to one embodiment of this invention. The centrifugal rotor 100 includes a rotor body 101, e.g. a solid disk, to be used under centrifugal force, e.g. mounted in a centrifuge. There are several chambers designed within the rotor body 101 for delivering and/or analyzing biological samples, e.g. blood, urine, spinal fluid, semen and etc. In particular, a sample application chamber 106 and a diluent container 104 are designed closer to a center 101a of the rotor body 101 than the remaining chambers or cuvettes. A predetermined volume of diluents 114b (as illustrated in FIG. 2) can be pre-stored inside the diluent container 104. The biological sample, e.g. blood, can be manually deposited into the sample application chamber 106. A mixing chamber 108 is positioned radially outward from the sample application chamber 104 and the diluent container 106 such that the mixing chamber 108 is able to receive fluid from thereof under centrifugal force. A delivery channel 106a is interconnected between the sample application chamber 106 and the mixing chamber 108 for removing a fluid in the sample application chamber 106 under centrifugal force. Another delivery channel 104a is interconnected between the diluent container 104 and the mixing chamber 108 for removing a diluent in the diluent container 104 under centrifugal force. A distribution ring 110 is positioned radially outward from the mixing chamber 108 and connected with the mixing chamber 108 via a siphon 108a. After the biological sample, e.g. blood, and diluent are mixed in the mixing chamber 108, the rotor body 101 is stopped, i.e. no centrifugal force is applied, and the siphon 108a is primed to deliver the diluted biological sample to the distribution ring 110. In this embodiment, the distribution ring 110 is part of a circle, which is concentric to a circumference of the rotor body 101. That is, the distribution ring 110 and circumference of the rotor body 101 share a common center 101a.

At least one analysis unit 114 is arranged radially outward from the distribution ring 110. Each analysis unit 114 includes a splitting cuvette 114b and a react cuvette 114c. A metering channel 114a is interconnected between the distribution ring 110 and the splitting cuvette 114b. When the rotor body 101 is applied with a centrifugal force again, the distribution ring 110 distributes the diluted biological sample into each metering channel 114a first and leaves the rest into an excess fluid dump 112. A proper centrifugal force should be applied not to enable the biological sample in each metering channel 114a to penetrate through a valve 114e, i.e. a portion with smaller cross-sectional area, between each metering channel 114a and each splitting cuvette 114b.

Each splitting cuvette 114b can be further divided into three parts: a relatively shallow cuvette $114b_1$, relatively deep cuvette $114b_2$ and a neck $114b_3$ between thereof. The relatively deep cuvette $114b_2$ is positioned radially outward from the relatively shallow cuvette $114b_1$. The neck $114b_3$ has a smaller cross-sectional area than the relatively shallow cuvette $114b_1$ and relatively deep cuvette $114b_2$ has. When a proper centrifugal force is applied to the rotor body 101, a relatively heavy part of the biological sample, e.g. blood cells of the whole blood, can be deliver through the neck $114b_3$ and trapped within the relatively deep cuvette $114b_2$. The react cuvette 114c is connected with the relatively shallow cuvette $114b_1$ or the relatively deep cuvette $114b_2$ via a siphon 114d. A desired reagent may be pre-deposited within the react cuvette 114c for performing a desired biological analysis. In an alternate embodiment, the splitting cuvette 114b as illustrated in FIG. 1 can be replaced by the splitting cuvette 214a as illustrated in FIG. 4.

Figure 3:
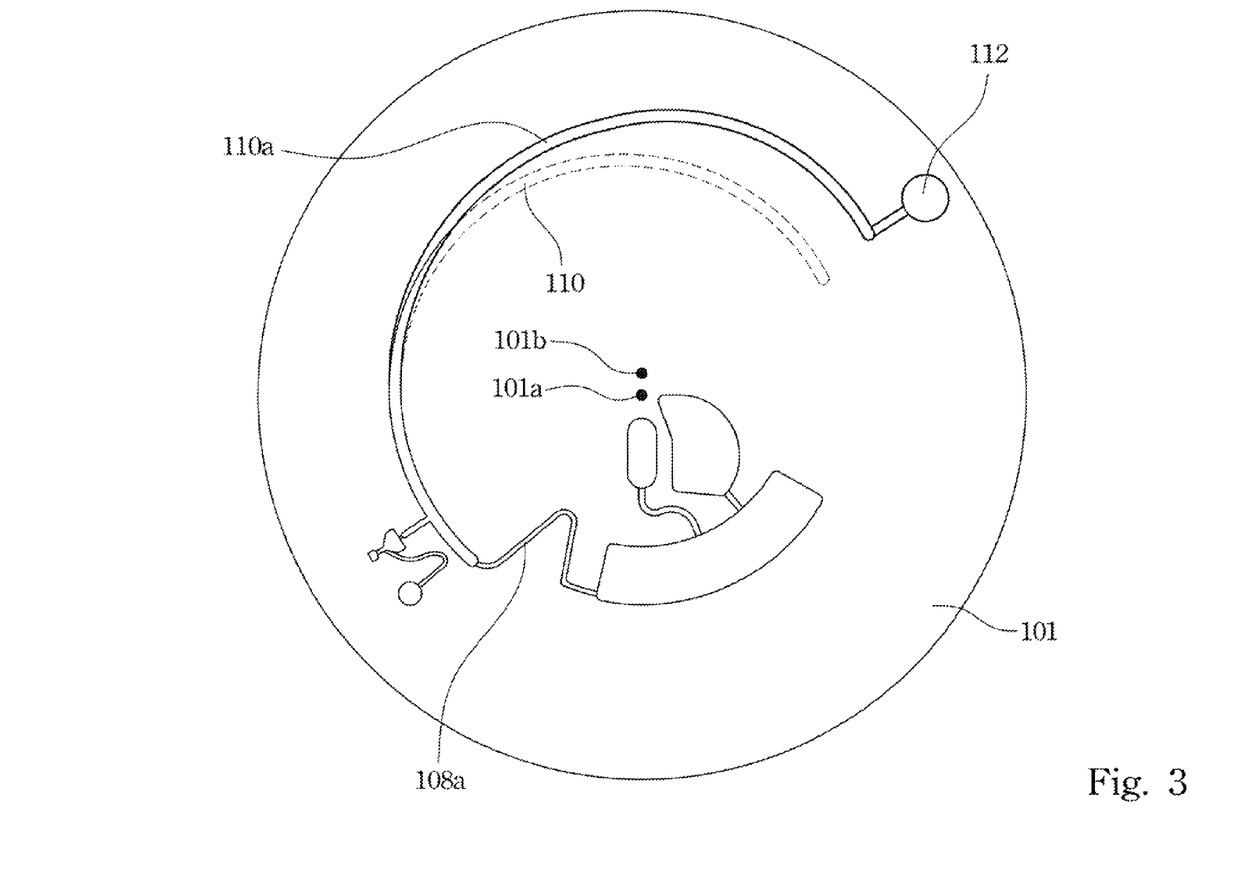
FIG. 3 illustrates a plan view of a centrifugal rotor according to another embodiment of this invention.

Referring to FIG. 3, which illustrates a plan view of a centrifugal rotor according to another embodiment of this invention. This embodiment is slightly different from the embodiment illustrated in FIG. 2 in that the distribution ring 110a is gradually radially outward from the distribution ring 110 of FIG. 2, from the end, connected to the siphon 108a, to the end, connected to the excess fluid dump 112. That is, the distribution ring 110a has the end, which is connected to the excess fluid dump 112, arranged radially outward from the other end, which is connected to the siphon 108a. In this embodiment, the distribution ring 110a is an arc with its corresponding center 101b different from the center 101a, which is a center of the distribution ring 110 and the rotor body 101. Besides, the distribution ring 110a is equipped with a larger radius than a radius of the distribution ring 110.

This design of the distribution ring is to avoid "trapping the sample within the distribution ring", thereby effectively routing excess sample into the excess dump. "The sample trapped within the distribution ring" may result in cosstalk between adjacent analysis units, splitting cuvettes or react cuvettes, e.g. reactant in a cuvette diffuses into another cuvette via the sample trapped within the distribution ring. The same design of the distribution ring can also be applied to other embodiments of this disclosure.

Figure 4:
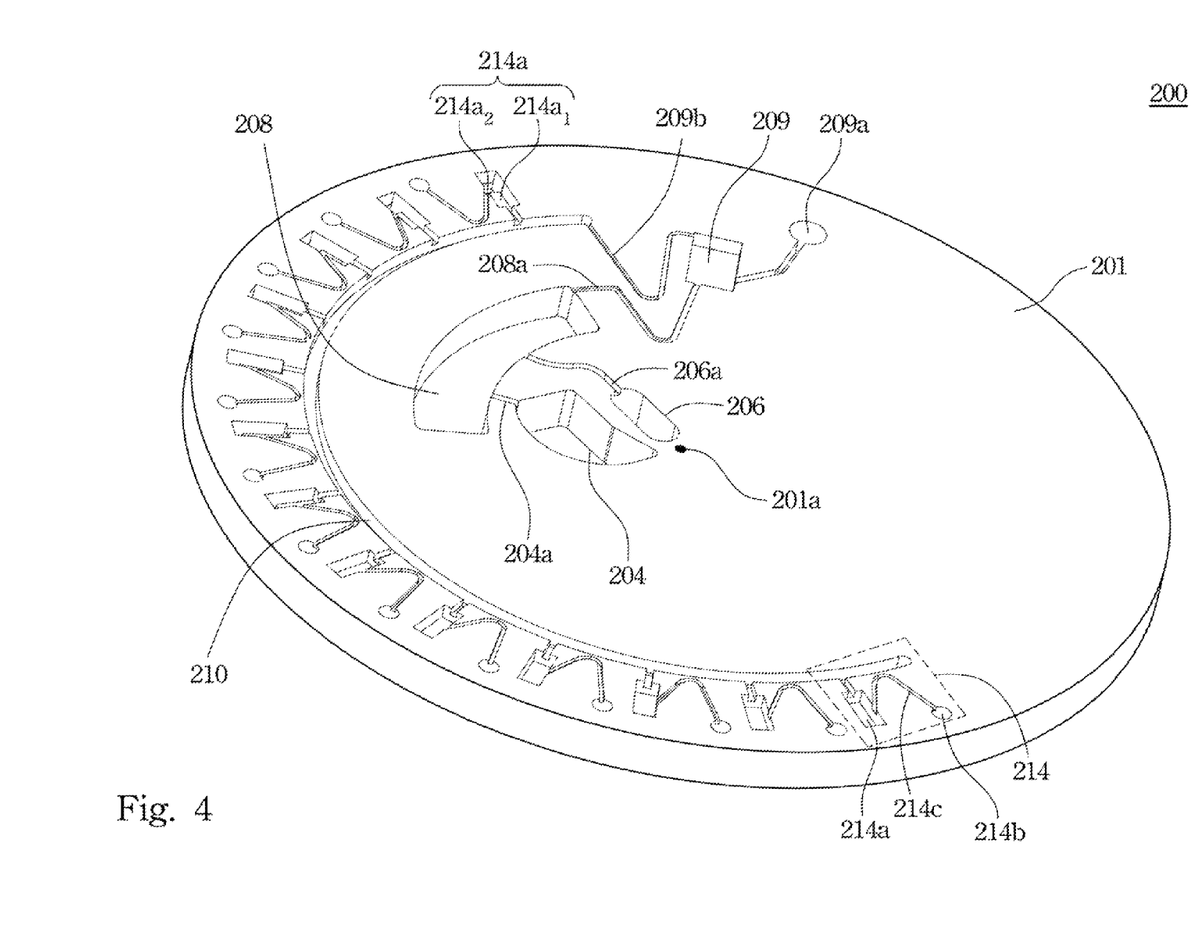
FIG. 4 illustrates a perspective view of a centrifugal rotor according to still another embodiment of this invention.
Figure 5:
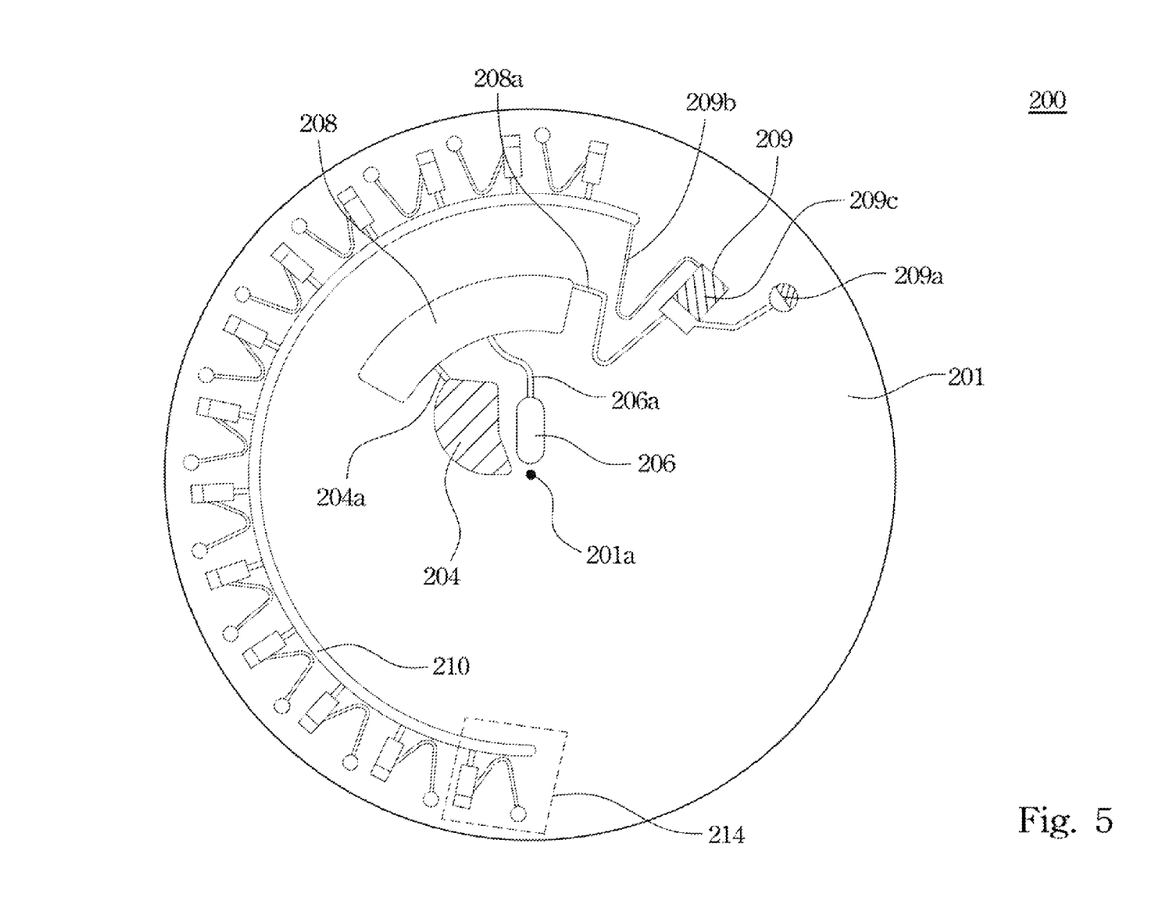
FIG. 5 illustrates a plan view of the centrifugal rotor in FIG. 4.
Figure 6:
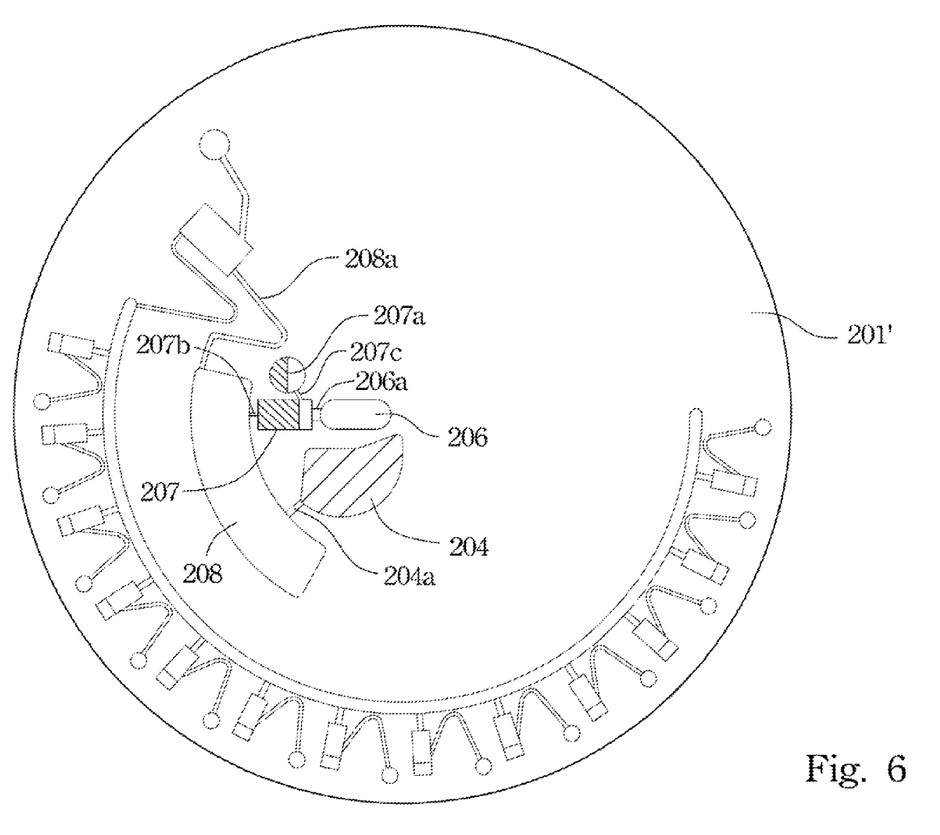
FIG. 6 illustrates a plan view of a centrifugal rotor according to still another embodiment of this invention.
Figure 7:
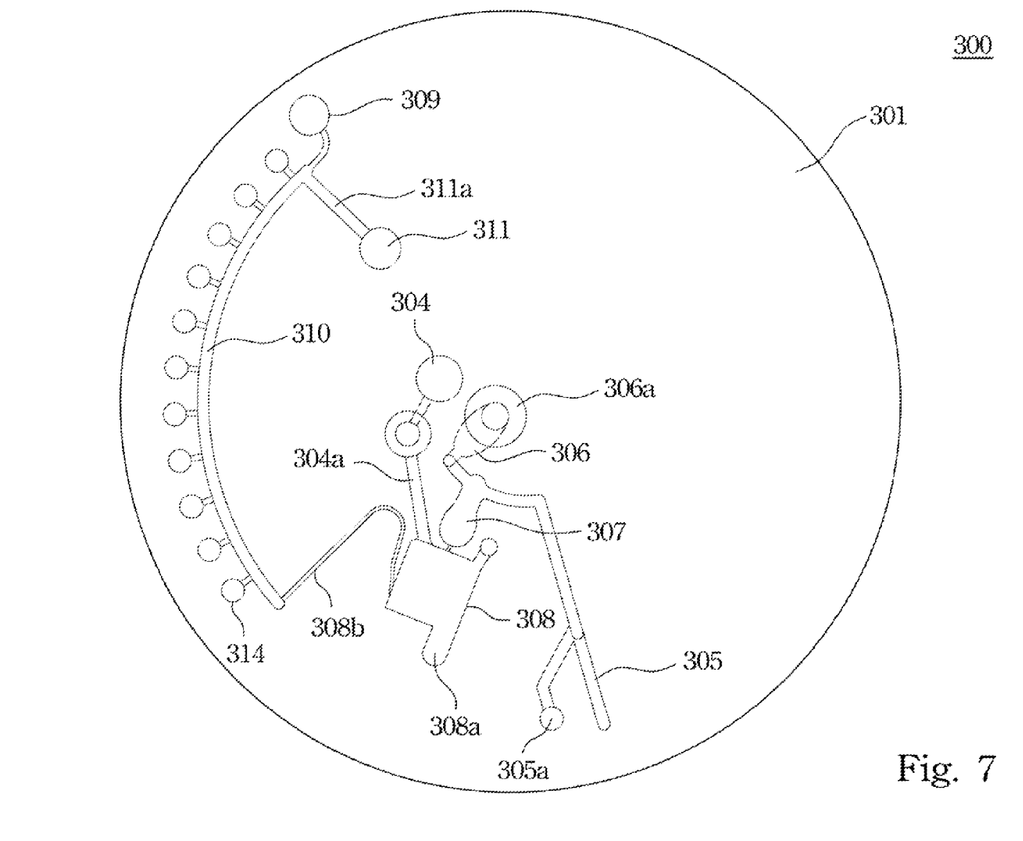
FIG. 7 illustrates a plan view of a centrifugal rotor according to still another embodiment of this invention.
Figure 8:
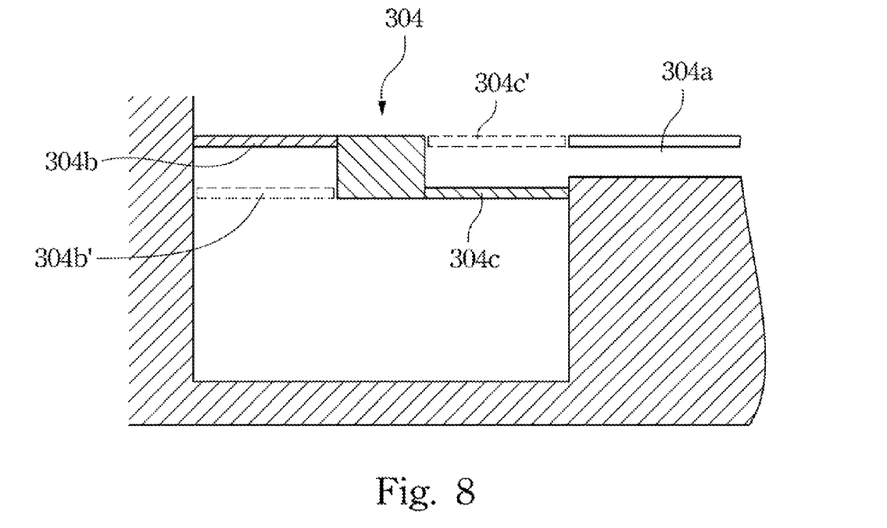
FIGS. 8 and 9 illustrate two examples of the diluent container as illustrated in FIG. 7.
Figure 9:
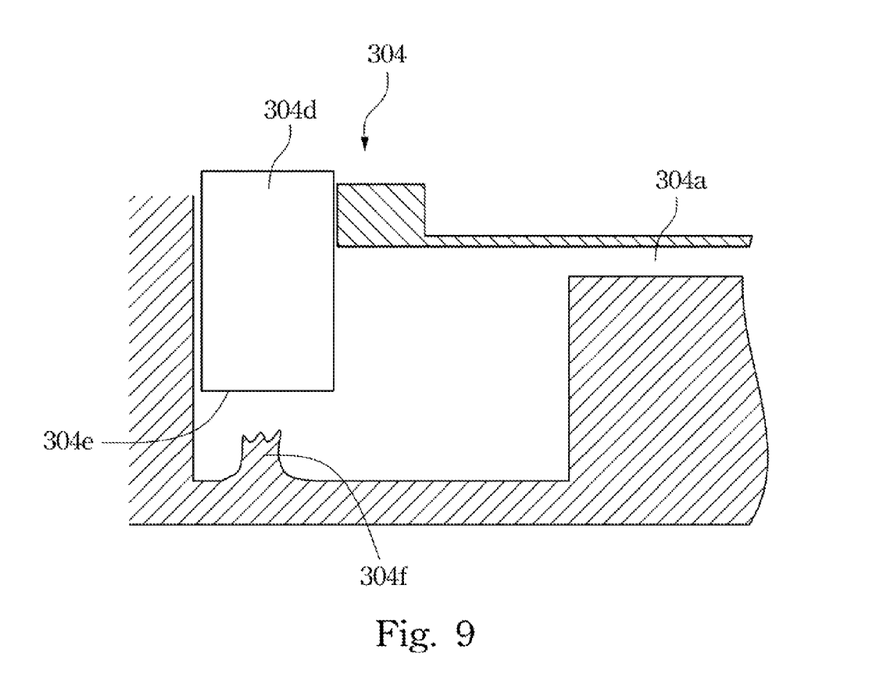

Referring FIG. 4 and FIG. 5, which respectively illustrate a perspective view and a plan view of a centrifugal rotor according to still another embodiment of this invention. The centrifugal rotor 200 includes a rotor body 201, e.g. a solid disk, to be used under centrifugal force, e.g. mounted in a centrifuge. There are several chambers designed within the rotor body 201 for delivering and/or analyzing biological samples, e.g. blood, urine, spinal fluid, semen and etc. In particular, a sample application chamber 206 and a diluent container 204 are designed closer to a center 201a of the rotor body 201 than the remaining chambers or cuvettes. A predetermined volume of diluents can be pre-stored inside the diluent container 204. The biological sample, e.g. blood, can be manually deposited into the sample application chamber 206. A mixing chamber 208 is positioned radially outward from the sample application chamber 204 and the diluent container 206 such that the mixing chamber 208 is able to receive fluid from thereof under centrifugal force. A delivery channel 206a is interconnected between the sample application chamber 206 and the mixing chamber 208 for removing a fluid in the sample application chamber 206 under centrifugal force. Another delivery channel 204a is interconnected between the diluent container 204 and the mixing chamber 208 for removing a diluent in the diluent container 204 under centrifugal force. A distribution ring 210 is positioned radially outward from the mixing chamber 208. A metering chamber 209 is interconnected between the mixing chamber 208 and the distribution ring 210. The metering chamber 209 is equipped with an excess fluid dump 209a. A siphon 208a is interconnected between the mixing chamber 208 and metering chamber 209. Another siphon 209b is interconnected between the distribution ring 210 and metering chamber 209. After the biological sample, e.g. blood, and diluent are mixed in the mixing chamber 208, the rotor body 201 is stopped, i.e. no centrifugal force is applied, and the siphon 208a is primed to deliver the diluted biological sample to the metering chamber 209. The rotor body 201 is then rotated again to meter a desired volume of the diluted biological sample and leave the rest to the excess fluid dump 209a. After the diluted biological sample is metered in the metering chamber 209, the rotor body 201 is stopped again, and the siphon 209b is primed to deliver the metered biological sample 209c to the distribution ring 210.

At least one analysis unit 214 is designed radially outward from the distribution ring 210. Each analysis unit 214 includes a splitting cuvette 214a and a react cuvette 214b. Since the desired volume of the diluted biological sample has been pre-metered before entering into the distribution ring 210, a metering channel, e.g. 114a in FIG. 2, may not be necessary in this embodiment. When the rotor body 201 is applied with a centrifugal force again, the distribution ring 210 distributes the diluted and metered biological sample into each splitting cuvette 214*a*.

Each splitting cuvette 214*a* can be further divided into two parts: a relatively shallow cuvette $\mathbf{214}a_1$ and a relatively deep cuvette $\mathbf{214}a_2$. The relatively deep cuvette $\mathbf{214}a_2$ is positioned radially outward from the relatively shallow cuvette $\mathbf{214}a_2$. When a proper centrifugal force is applied to the rotor body 201, a relatively heavy part of the biological sample, e.g. blood cells of the whole blood, can be moved into and trapped within the relatively deep cuvette $\mathbf{214}a_2$. The react cuvette 214*b* is connected with the relatively shallow cuvette $\mathbf{214}a_1$ or the relatively deep cuvette $\mathbf{214}a_2$ via a siphon 214*c*. A desired reagent may be pre-deposited within the react cuvette 214*b* for performing a desired biological analysis. In an alternate embodiment, the splitting cuvette 214*a* as illustrated in FIG. 4 can be replaced by the splitting cuvette 114*b* as illustrated in FIG. 1.

Referring to FIG. 6, which illustrates a plan view of a centrifugal rotor according to still another embodiment of this invention. This embodiment is slightly different from the embodiment illustrated in FIG. 5 in that another metering chamber 207 is interconnected between the mixing chamber 208 and the sample application chamber 206. The metering chamber 207 is also equipped with an excess fluid dump 207*a* (using a delivery channel 207*c* to interconnect between thereof). A delivery channel 206*a* is interconnected between the metering chamber 207 and the application sample chamber 206 for removing a sample fluid in the application sample chamber 206 under centrifugal force. A delivery channel 207*b* is interconnected between the metering chamber 207 and the mixing chamber 208 for removing the sample fluid in the metering chamber 207 under centrifugal force. In this embodiment, the delivery channel 206*a* has a larger cross-sectional area than the delivery channel 207*b* has, and the delivery channel 207*c* has a larger cross-sectional area than the delivery channel 207*b* has. Therefore, when a proper centrifugal force is applied to the rotor body 201', the biological sample can be metered in the metering chamber 207 before entering into the mixing chamber 208. Besides, the delivery channel 206*a* has a larger cross-sectional area than the delivery channel 204*a* has. Thus, if a proper centrifugal force is applied to the rotor body 201', the diluent in the diluent container 204 does not enter into the mixing chamber 208 when the biological sample enters into the metering chamber 207. The metering chamber 207 is designed to meter a desired volume of the undiluted biological sample so as to control a mixed ratio of the biological sample and diluent, which is pre-stored in the diluent container 204.

Referring to FIG. 7, which illustrates a plan view of a centrifugal rotor according to still another embodiment of this invention. The centrifugal rotor 300 includes a rotor body 301, e.g. a solid disk, to be used under centrifugal force, e.g. mounted in a centrifuge. There are several chambers designed within the rotor body 301 for delivering and/or analyzing biological samples, e.g. blood, urine, spinal fluid, semen and etc. In particular, a sample application chamber 306 (equipped with a sample filling opening 306*a*) and a diluent container 304 are designed closer to a center of the rotor body 301 than the remaining chambers or cuvettes. The biological sample, e.g. blood, can be manually deposited into the sample application chamber 306 through the sample filling opening 306*a*. A metering chamber 307 is positioned radially outward from the sample application chamber 306 to pre-measure the sample, e.g. whole blood, before entering a mixing and splitting chamber 308. Excess sample is routed to a metering chamber 305 and an excess dump 305*a* when a centrifugal force is applied. The mixing and splitting chamber 308 is positioned radially outward from the sample application chamber 304 and the diluent container 306 such that the mixing and splitting chamber 308 is able to receive fluid from thereof under centrifugal force. The mixing and splitting chamber 308 performs both "mixing the sample with the diluent" and "splitting the diluted sample into two parts". A relatively heavier part of the diluted sample, e.g. blood cells of the whole blood, will be routed to and trapped within a chamber tail 308*a*, e.g. a relatively deeper area compared with the remaining area of the mixing and splitting chamber, under centrifugal force. A distribution ring 310 is positioned radially outward from the mixing and splitting chamber 308 and connected with the mixing and splitting chamber 308 via a siphon 308*b*. After the biological sample, e.g. blood, and diluent are mixed and split in the mixing and splitting chamber 308, the rotor body 301 is stopped, i.e. no centrifugal force is applied, and the siphon 308*b* is primed to deliver a relatively lighter part of the diluted sample, e.g. diluted plasma of the whole blood, to the distribution ring 310. With the mixing and splitting chamber 308, the sample can be effectively used with the less sample wasted (compared with the mixing function and splitting function are executed by two separate chambers). For example, if 35 μl whole blood is split first and then mixed with 500 μl diluent by two separate chambers, only about 17 μl blood plasma can be extracted. Deducting the volume wasted in siphon and splitting chamber (about 4 μl), only 13 μl blood plasma can be effectively used. With the mixing and splitting chamber 308, 35 μl whole blood plus 500 μl diluent are mixed and split in the same chamber, only 4 μl diluted blood wasted in siphon and splitting chamber. More percentage of 35 μl whole blood can be effectively used. The distribution ring 310 has two ends to be respectively connected with the siphon 308*b* and an excess dump 309. A plurality of react cuvettes 314 are positioned radially outward from and connected with the distribution ring 310. When the rotor body 301 is applied with a centrifugal force again, the distribution ring 310 distributes the relatively lighter part of the diluted sample into each react cuvette 314 first and leaves the rest into the excess fluid dump 309. The distribution ring 310 may be equipped a vent hole 311, and a vent channel is interconnected between the vent hole 311 and the distribution ring 310.

In an alternate embodiment, the react cuvette 314 can be replaced by the analysis unit 114 as illustrated in FIG. 1, the analysis unit 214 as illustrated in FIG. 4, or the analysis units (414, 415) as illustrated in FIG. 10.

FIGS. 8 and 9 illustrate cross-sectional views of two examples of the diluent container as illustrated in FIG. 7. FIG. 8 illustrates a piston-regulated diluent container 304 with two pistons (304*b* and 304*c*) movably sealing the chamber, thereby sealing the diluent under thereof. When a force applied to the piston 304*b*, the piston 304*b* is moved downwards (illustrated as 304*b*') while the piston 304*c* is moved upwards (illustrated as 304*c*'). Therefore, the diluent can be flowed out through a channel 304*a*. FIG. 8 illustrates the diluent container 304 equipped with an extra aluminum sealed diluent container 304*d*. The aluminum sealed diluent container 304*d* is vertically slidable within the diluent container 304. When a force applied to the diluent container 304*d*, the diluent container 304*d* is moved downwards and its aluminum seal 304*e* can be broken by a convex member 304*f*. Therefore, the diluent can be flowed out of the diluent container 304*d* and routed to the mixing and splitting chamber through the channel 304*a*.

Referring to FIG. 10, which illustrates a plan view of a centrifugal rotor according to still another embodiment of this invention. The centrifugal rotor 400 includes a rotor body 401, e.g. a solid disk, to be used under centrifugal force, e.g. mounted in a centrifuge. There are several chambers designed within the rotor body 401 for delivering and/or analyzing biological samples, e.g. blood, urine, spinal fluid, semen and etc. In particular, a sample application chamber 406 and a diluent container 404 are designed closer to a center of the rotor body 401 than the remaining chambers or cuvettes. A metering chamber 407 is interconnected between a mixing chamber 408 and the sample application chamber 406. The metering chamber 407 is also equipped with an excess fluid dump 407a (using a delivery channel to interconnect between thereof). This embodiment is different from the above-discussed embodiments in that the delivery channel between chambers is equipped with a bubble-enhanced valve or sacrificed valve. For example, a delivery channel 404a has a sacrificed valve, which has a removable solid block within the delivery channel to be removed by a user. When the solid block is removed, the delivery channel 404a becomes a normal delivery channel. For example, a delivery channel 407b has a bubble-enhanced valve. By "bubble-enhanced valve", it means "a valve of a shape to trap a bubble within the delivery channel when a liquid flow passes by, wherein the bubble is able to regulate the flow rate of the delivery channel".

Figure 10:
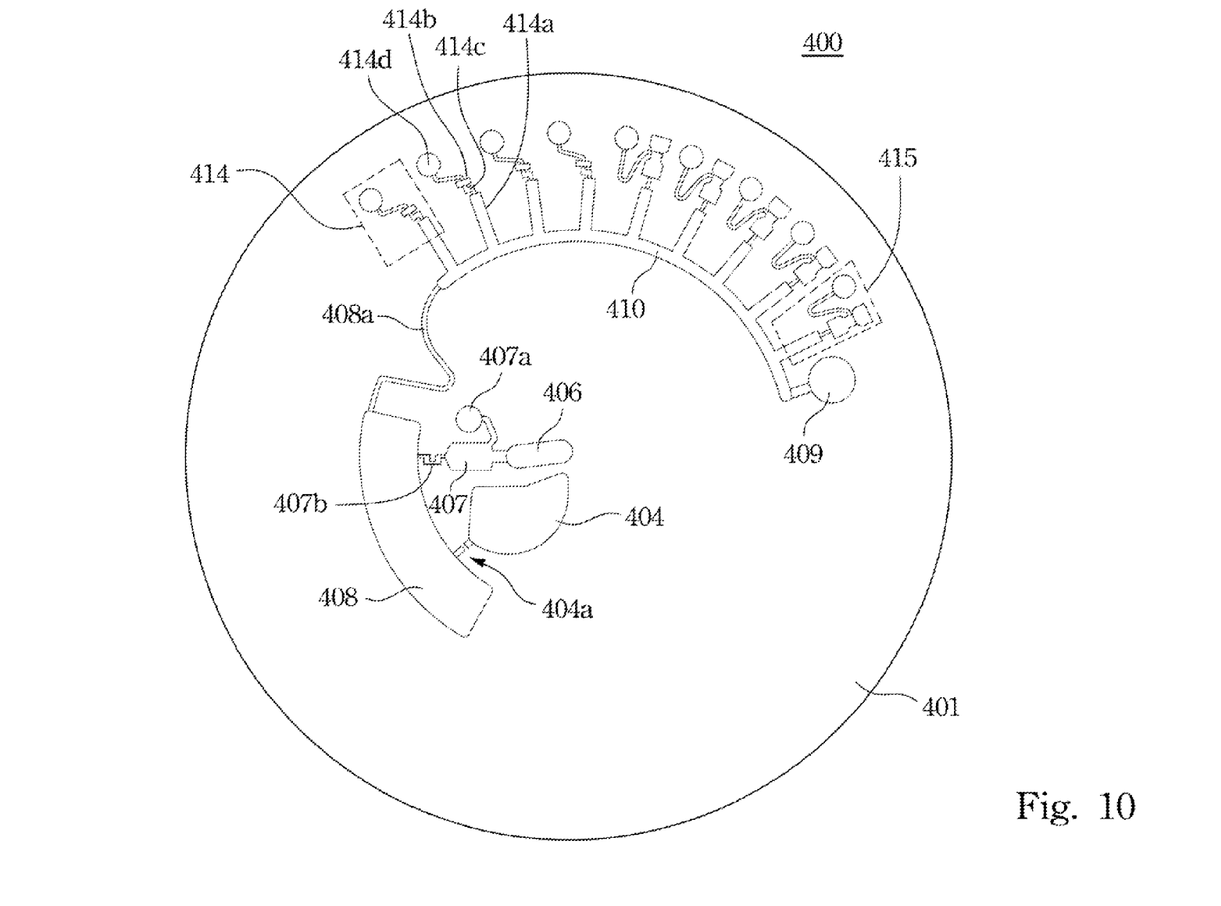
FIG. 10 illustrates a plan view of a centrifugal rotor according to still another embodiment of this invention.

The distribution ring 410 has two ends to be respectively connected with the siphon 408b and an excess dump 409. Two types of analysis units (414, 415) are positioned radially outward from and connected with the distribution ring 410. When the rotor body 401 is applied with a centrifugal force again, the distribution ring 410 distributes the diluted sample into each analysis unit (414, 415) first and leaves the rest into the excess fluid dump 409. The analysis unit 415 is almost the same as the design of the analysis unit 114 as illustrated in FIG. 1 and FIG. 2 except some shape variants. The analysis unit 414 includes a splitting cuvette and a react cuvette 414d. The splitting cuvette includes a metering channel 414a, a cuvette 414b and a bubble-enhanced valve 414c interconnected therebetween. When the rotor body 301 is applied with a centrifugal force, the relatively lighter part of the diluted sample will be routed to the cuvette 414b and further routed to the react cuvette 414d for a desirable reaction.

Figure 11:
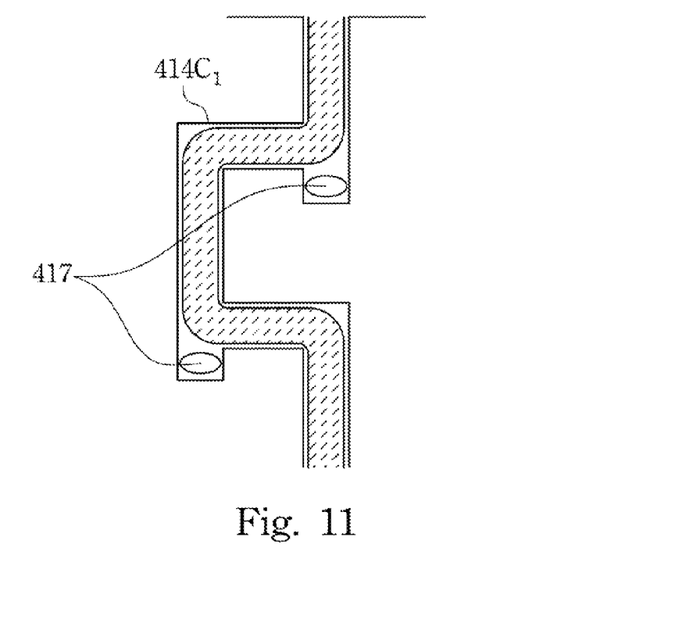
FIGS. 11 and 12 illustrate two examples of the bubble-enhanced valve as illustrated in FIG. 10.
Figure 12:
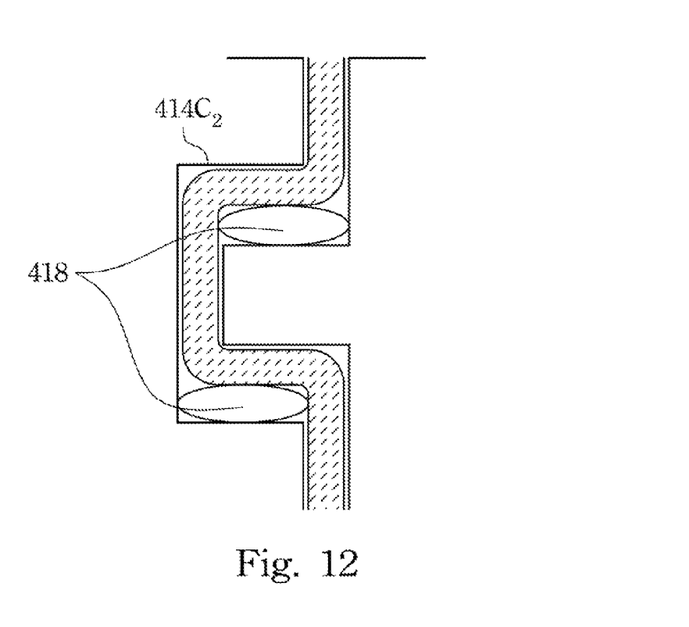

FIGS. 11 and 12 illustrate two examples of the bubble-enhanced valve as illustrated in FIG. 10. The bubble-enhanced valve $414c_1$ includes dead areas, where air can be easily trapped to form bubbles, and the bubbles 417 tend to regulate the flow rate of the passing liquid, i.e. slow or stop the flow rate of the passing liquid. The bubble-enhanced valve $414c_2$ includes widened channel to create dead areas, where air can be easily trapped to form bubbles, and the bubbles 418 tend to regulate the flow rate of the passing liquid, i.e. slow or stop the flow rate of the passing liquid. The bubble-enhanced valve should be functioned along with a centrifugal force to control the passing liquid through a delivery channel.

According to the above-discussed embodiment, the centrifugal rotor attempts to split a biological sample, which comprises biological cellular components and biological fluids, into separate parts under centrifugal force after the biological sample being diluted, metered and distributed. An advantage to design such centrifugal rotor is to reduce a required volume of a biological sample to be filled into the sample application chamber. Another advantage to design such centrifugal rotor is to allow a relatively larger tolerance for actual size's precision of chambers such that the centrifugal rotor is amenable to low-cost manufacturing procedures.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A centrifugal rotor comprising:
   a rotor body comprising:
      a sample application chamber;
      a diluent container comprising diluents inside thereof;
      a mixing and splitting chamber disposed radially outward from the sample application chamber and the diluent container for receiving fluid from thereof, wherein the mixing and splitting chamber comprises a chamber tail disposed radially outward from the remaining area of the mixing and splitting chamber, the chamber tail is a relatively deeper area compared with the remaining area of the mixing and splitting chamber;
      a first metering chamber interconnected between the mixing and splitting chamber and the sample application chamber, wherein the first metering chamber is disposed radially outward from the sample application chamber;
      a second metering chamber disposed radially outward from and connected with the first metering chamber;
      a first excess dump connected with the second metering chamber;
      a distribution ring disposed radially outward from the mixing and splitting chamber, and connected with the mixing and splitting chamber via a first siphon, wherein an inlet of the first siphon is disposed at a corner of the mixing and splitting chamber, which is different from a corner of the mixing and splitting chamber where the chamber tail is disposed, and the chamber tail is radially outward from the inlet of the first siphon; and
      at least one react cuvette disposed radially outward from and connected with the distribution ring.

2. The centrifugal rotor of claim 1, further comprising a metering channel interconnected between the distribution ring and the react cuvette.

3. The centrifugal rotor of claim 2, further comprising a valve interconnected between the metering channel and the react cuvette, wherein the valve is a bubble-enhanced valve, a sacrificed valve or a valve having a cross-section smaller than a cross-section of the metering channel and the react cuvette.

4. The centrifugal rotor of claim 1, further comprising a second excess fluid dump, wherein the distribution ring is interconnected between the first siphon and the second excess fluid dump.

5. The centrifugal rotor of claim 1, further comprising:
   a first delivery channel interconnected between the first metering chamber and the mixing and splitting chamber for removing a fluid in the first metering chamber under centrifugal force; and
   a second delivery channel interconnected between the diluent container and the mixing and splitting chamber for removing a diluent in the diluent container under centrifugal force,
   wherein the first delivery channel comprises a bubble-enhanced valve, a sacrificed valve or a valve having, a cross-section smaller than a cross-section of the first metering chamber and the mixing and splitting chamber, and the second delivery channel comprises a sacrificed valve, a bubble-enhanced valve or a valve having a cross-section smaller than a cross-section of the diluent container and the mixing and splitting chamber.

6. The centrifugal rotor of claim 1, wherein the diluent container is a piston-regulated chamber.

7. The centrifugal rotor of claim 1, wherein the diluent container is an aluminum sealed diluent container.

8. The centrifugal rotor of claim 1, wherein the distribution ring comprises two opposite first end and second end, the first end is connected to the first siphon, the second end is connected to the second excess fluid dump, the second end is radially outward from the first end.

9. The centrifugal rotor of claim 8, wherein the distribution ring is an arc with a corresponding center different from a center of the rotor body.

10. The centrifugal rotor of claim 1, wherein the distribution ring is part of a circle, which is concentric to a circumference of the rotor body.

11. The centrifugal rotor of claim 1, further comprising at least one splitting cuvette disposed radially outward from the distribution ring, the splitting cuvette comprising:
    a relatively shallow cuvette; and
    a relatively deep cuvette disposed radially outward from the relatively shallow cuvette.

12. The centrifugal rotor of claim 11, further comprising a metering channel interconnected between the distribution ring and the splitting cuvette.

13. The centrifugal rotor of claim 12, further comprising a valve interconnected between the metering channel and the splitting cuvette, wherein the valve is a bubble-enhanced valve, a sacrificed valve or a valve having a cross-section smaller than a cross-section of the metering channel and the splitting cuvette.

14. The centrifugal rotor of claim 13, wherein the splitting cuvette further comprises a neck, which has a smaller cross-sectional area than the relatively shallow cuvette and relatively deep cuvette has, interconnected between the relatively shallow cuvette and relatively deep cuvette.

15. A centrifugal rotor comprising:
    a rotor body comprising:
        a sample application chamber;
        a diluent container comprising diluents inside thereof;
        a mixing and splitting chamber disposed radially outward from the sample application chamber and the diluent container for receiving fluid from thereof, wherein the mixing and splitting chamber comprises a chamber tail disposed radially outward from the remaining area of the mixing and splitting chamber, the chamber tail is a relatively deeper area compared with the remaining area of the mixing and splitting chamber;
        a first metering chamber interconnected between the mixing and splitting chamber and the sample application chamber, wherein the first metering chamber is disposed radially outward from the sample application chamber;
        a second metering chamber disposed radially outward from and connected with the first metering chamber;
        a first excess dump connected with the second metering chamber;
        a distribution ring disposed radially outward from the mixing and splitting chamber, and connected with the mixing and splitting chamber via a first siphon, wherein the distribution ring comprises two opposite first end and second end, the first end is connected to the first siphon, the second end is connected to the second excess fluid dump, the distribution ring is gradually radially outward from the first end to the second end, an inlet of the first siphon is disposed at a corner of the mixing and splitting chamber, which is different from a corner of the mixing and splitting chamber where the chamber tail is disposed, and the chamber tail is radially outward from the inlet of the first siphon; and
    at least one react cuvette disposed radially outward from and connected with the distribution ring.

16. A centrifugal rotor comprising:
    a rotor body comprising:
        a sample application chamber;
        a diluent container comprising diluents inside thereof;
        a mixing and splitting chamber disposed radially outward from the sample application chamber and the diluent container for receiving fluid from thereof;
        a first metering chamber interconnected between the mixing and splitting chamber and the sample application chamber, wherein the first metering chamber is disposed radially outward from the sample application chamber;
        a second metering chamber disposed radially outward from and connected with the first metering chamber;
        a first excess dump connected with the second metering chamber;
        a distribution ring disposed radially outward from the mixing and splitting chamber, and connected with the mixing and splitting chamber via a first siphon, wherein the distribution ring is gradually radially outward from the first end to the second end, and the distribution ring is an arc with a corresponding center different from a center of the rotor body; and
    at least one react cuvette disposed radially outward from and connected with the distribution ring.

* * * * *